United States Patent [19]

Kruse et al.

[11] 4,326,072
[45] Apr. 20, 1982

[54] RUTHENIUM CATALYZED HYDROGENATION OF D-GLUCURONIC ACID

[75] Inventors: Walter M. Kruse; Makram H. Meshreki, both of Wilmington, Del.

[73] Assignee: ICI Americas Inc., Wilmington, Del.

[21] Appl. No.: 165,210

[22] Filed: Jul. 1, 1980

[51] Int. Cl.$^3$ ............................................. C07C 59/105
[52] U.S. Cl. ..................... 562/587; 568/862; 568/863; 260/343.6; 252/460
[58] Field of Search ................ 562/587; 568/862, 863; 260/343.6

[56] References Cited

U.S. PATENT DOCUMENTS 1,915,431 6/1933 Lautenschläger ................. 568/863
3,336,239 8/1967 Bailey et al. ........................ 568/862

FOREIGN PATENT DOCUMENTS 453324 12/1948 Canada ............................... 568/862

Primary Examiner—Paul J. Killos
Attorney, Agent, or Firm—David J. Levy; John M. Sheehan

[57] ABSTRACT

A method for the synthesis of L-gulonic acid by catalytically hydrogenating D-glucuronic acid utilizing a ruthenium-based catalyst.

9 Claims, No Drawings

RUTHENIUM CATALYZED HYDROGENATION OF D-GLUCURONIC ACID

BACKGROUND OF THE INVENTION

The present invention relates to a process for the hydrogenation of D-glucuronic acid to yield L-gulonic acid.

L-gulonic acid, the preparation of which is an object of the present invention, is valuable as an intermediate in the preparation of xylitol. In a representative procedure, L-gulonic acid may be oxidatively decarboxylated by a Ruff degradation of yield L-xylose as described in references including E. Fisher, O. Ruff, Ber. 33 2142 (1900). The L-xylose obtained may be reduced to xylitol by methods described or referred to in U.S. Pat. No. 4,075,406 or described, with reference to the reduction of glucose to sorbitol, by L. W. Wright in Chemtech, January, 1974, p.42.

The reduction of D-glucuronic acid to yield L-gulonic acid with sodium amalgam in a weakly alkaline solution was reported by Thierfelder in Z. Physiol. Chem., 15, 71 (1891). A similar reduction of sodium D-glucuronate monohydrate utilizing sodium borohydride as the reagent is described by M. L. Wolfrom and K. Anno in J. Am. Chem. Soc., 74, 5583 (1952). In a somewhat different procedure, a sodium borohydride reduction of D-glucuronolatcone resulted in preferential reduction of the carboxyl, rather than the aldehydic, group, see D. L. MacDonald and H. O. L. Fischer, J. Am. Chem. Soc. 78, 5025 (1956).

Catalytic hydrogenation of D-glucuronic acid using a nickel catalyst was reported in Example 4 of German Patentschrift No. 618,907 issued Sept. 5, 1935. However, as demonstrated in the Comparative Examples which follow, use of nickel will require a relatively high temperature which causes degradation of the starting material. Nickel catalysts often require reprocessing after use since they may be deactivated during or after the reaction. Therefore, nickel has disadvantages as a catalyst in continuous processing.

A further teaching in the art of the reduction of D-glucuronolactone with a nickel catalyst to yield L-gulonolactone is found in the article "A New Action of Anion Exchange Resins on the Lactone Ring of Some Carbohydrates" by Ishidate, et al appearing in Chem. Pharm. Bull. 13(2) pages 173-176 (1965). However the starting material was only used in a concentration of about 10% by weight of the solution at room temperature. Further, the workup of the product was complicated in that after filtration of the catalyst, the filtrate was concentrated to a syrup and crystals were formed by the addition of dry ethanol.

It is an object of the invention to provide a relatively low temperature reaction route from D-glucuronic acid to L-gulonic acid whereby a product is obtained which freely crystalizes from solution after partial evaporation in high yield and with a minimum of by-products which would complicate recycling of unreacted starting material. It is also an object of this invention to provide a continuous catalytic process for the preparation of L-gulonic acid from D-glucuronic acid whereby the catalytic hydrogenation catalyst may be utilized for long periods of time without catalyst reactivation. It is also an object of the invention to provide an economical process for the preparation of L-gulonic acid in terms of energy input, durability of catalyst cost of separating product and of discarding by-products.

A further object of the invention is a process for the production of L-gulonic acid from a concentrated solution of the starting material, thus resulting in a more economical use of facilities.

SUMMARY OF THE INVENTION

An improved process for the preparation of L-gulonic acid from D-glucuronic acid by catalytic hydrogenation with a ruthenium catalyst.

DETAILED DESCRIPTION OF THE INVENTION

As used in the present invention, the term "D-glucuronic acid," used as the starting material of the invention, is indicative of any or all of the compounds represented by the following formulae (I) through (IV):

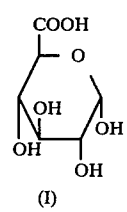
(I)

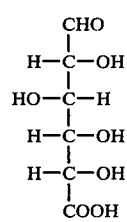
(II)

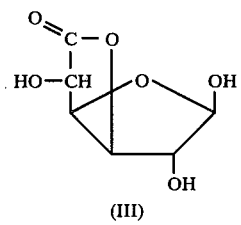
(III)

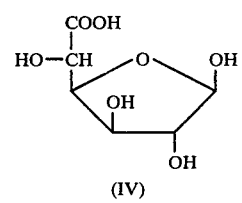
(IV)

The compound represented by formula (I) is the pyranose form of D-glucuronic acid and may be referred to as D-glucopyranuronic acid or D-glucopyranosyluronic acid.

The compound represented by formula (II) is the open chain form of the D-glucuronic acid.

The compound represented by formula (II) is the furanose form of D-glucuronic acid and may be referred to as D-glucofuranuronic acid, D-glucuronolactone, D-glucofuranurono-6,3-lactone or D-glucurone, although other names have been used.

The compound represented by formula (IV) is the free acid form of the compound of formula (III).

In solution, and particularly in water, compounds of formulae (I) through (IV), which may be discreet entities as crystals, nevertheless coexist by an equilibrium between the species. The actual species which is hydrogenated by the process of the invention is probably the open chain of formula (II). However, any of the compounds of formulae (I) through (IV) which are available as a solid or even as a mixture thereof, may be used as the starting material for the process of the present invention. A more detailed explanation of the equilibrium is available in "Glucuronic Acid, Free and Combined," edited by G. J. Dutton (Academic Press, New York, 1966).

A preferred source of D-glucuronic acid starting material is the compound having formula (III) which is available commerically from Pfanstiehl Laboratories, Inc. of Waukegan, Illinois, under the name D-glucurono-6,3-lactone or from Aldrich Chemical Company, Inc. of Milwaukee, WIS., under the name D-glucurono-3,6-lactone. The choice of the lactone of formula (III) as the starting material is made in view of its excellent stability which allows an accurate molar measurement in preparation for the reaction.

The product of the invention process is "L-gulonic acid," which term is meant to denote the open chain form of the following formula (V) and the 1,4-lactone of the following formula (VI):

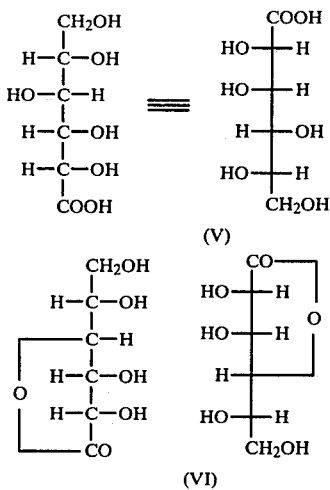

The catalysts for use in the present invention are those containing ruthenium metal. Preferably, such ruthenium metal catalysts comprise a support and the ruthenium metal itself. Examples of suitable supports include aluminosilicate zeolites, aluminosilicate clays, alumina, silica (including forms of silica such as kieselguhr, diatomaceous earth and synthetic gels) and types of elemental carbon such as carbon black. Examples of the aluminosilicate zeolite ruthenium metal catalysts are those described in U.S. Pat. No. 3,963,788. Suitable aluminosilicate clay ruthenium metal catalysts are described in U.S. Pat. No. 3,963,789. Other ruthenium catalysts which may be used in the present invention are those described in U.S. Pat. No. 2,868,847 issued Jan. 13, 1959 which teaches the catalytic hydrogenation of sugars. A preferred support is carbon black in view of its high surface area. In general ruthenium catalysts having from about 0.1 to about 5% by weight ruthenium metal may be used in the process of the present invention.

Ruthenium catalysts comprising a zeolite support for use in the process of this invention are crystalline or essentially crystalline aluminosilicate zeolites of the molecular sieve type having a silica/alumina mol ratio of at least 3 and containing a minor catalytically effective amount of ruthenium. The preferred zeolites are synthetic. The ruthenium content of the catalyst is in the range of about 0.1% to about 5%, preferably about 0.5% to about 3%, of the total catalyst weight. The ruthenium is present as the free metal finely dispersed on the surface of the zeolite, which serves as a support.

The zeolites are crystalline aluminosilicates in which the aluminum, silicon, and oxygen atoms are arranged in a rigid three-dimensional network having internal cavities of molecular size and pores of uniform size which provide access to these cavities. The crystal network includes $SiO_4$ and $AlO_4$ tetrahedra; the electro-negativity of the latter is balanced by cation (e.g., metal ions, ammonium ions, or hydrogen ions). The crystal structure of zeolites has been discussed extensively in the literature.

Particular ruthenium-containing zeolites are the ruthenium metal-loaded Y type zeolite catalysts. Y type zeolites are characterized by a silica/alumina mol ratio of at least about 3, and effective pore size of at least about 8 Angstrom units in the hydrogen form, and a three-dimensional network of channels. Examples of catalysts of this type are ruthenium on Ultrastable Faujasite Y (hydrogen form), ruthenium on zeolite Y (hydrogen form), and ruthenium on calcined zeolite SK-89. Ultrastable faujasite Y (hydrogen form) is commerically available from the Davison Chemical Division of W. R. Grace and Company and is described in U.S. Pat. No. 3,293,192 and in C. V. McDaniel and P. K. Maher, Society of Chemical Industry (London) Monograph No. 186 (1968); P. K. Maher, F. D. Hunter, and J. Scherzer, "Molecular Sieves," Advances in Chemistry Series No. 101 (American Chemical Society), pages 266–276 (1971); J. Scherzer and J. L. Bass, Journal of Catalysts, 28, pp. 101–115 (1973). According to U.S. Pat. No. 3,293,192, the "ultrastable" zeolite described therein has a silica/alumina mol ratio of about 3.5 to 7, and an alkali metal content less than 1%. This zeolite is prepared in the hydrogen form, but can be converted to other cationic forms; among the cations mentioned in the patent are platinum "and other Group VIII" metal ions (no Group VIII metals other than platinum are specifically named). Zeolite Y (hydrogen or "decationized" form) is commerically available from Linde Division of Union Carbide Corporation, New York, NY, and is described in U.S. Pat. No. 3,130,006. Both ultrastable faujasite Y (hydrogen form) and zeolite Y (hydrogen form) can be synthesized from the sodium form of zeolite Y. Ultrastable faujasite Y is a material of improved thermal stability in which a portion of the aluminum originally present in the zeolite crystal structure has been removed. Another high desirable Y type zeolite catalyst is ruthenium on calcined zeolite SK-89. Zeolite SK-89 is available from Linde Division of Union Carbide Corporation.

Ruthenium-containing zeolite catalysts which may be used in the process of this invention may be prepared from the corresponding zeolites in the hydrogen form by ion exchange with an aqueous solution of a simple ruthenium salt, e.g. ruthenium trichloride, followed by reduction of ruthenium to the metallic state. A simple ruthenium salt, rather than a complex salt (e.g., a ruthenium ammine salt), should be used. Ion exchange may be accomplished by known techniques, e.g. suspending particles of the zeolite (hydrogen form) in an aqueous slurry with stirring for a time sufficient to effect ion exchange, and then separating the ruthenium/zeolite particles from solution by conventional means such as filtration and drying the ruthenium/zeolite particles. This gives the unreduced form of the catalyst, in which ruthenium is present as a cation in the trivalent state. The reduced form may be prepared by reducing the ruthenium cation to the metallic state with hydrogen in the dry state at a temperature of about 50° C. to about 150° C. Conveniently, this step may be done simultaneously with the process of the present invention, i.e. during the hydrogenation of D-glucuronic acid.

Ruthenium catalysts comprising a clay support used in the process of this invention comprise ruthenium on a crystalline aluminosilicate clay. The catalysts contain from about 0.1% to about 5%, preferably from about 0.5% to about 3% by weight of ruthenium, based on total catalyst weight. The ruthenium is present as the free metal finely dispersed on the surfaces of the clay, which serves as a support or carrier.

The clay minerals which are used in preparing the catalysts for the invention are hydrated crystalline aluminosilicates which have sheet or layer structures and which have base exchange capacity. These clays characteristically have a crystal structure which includes one or more tetrahedral silica layers and one or more octahedral alumina layers, with a variable amount of water and metal cations such as sodium, magnesium and calcium associated with the crystal lattice in cation or base exchange relationship. These layers are essentially two-dimensional sheet-like structures. Part of the silicon in the tetrahedral layer may be replaced by aluminum, and part of the aluminum may be replaced by other metals such as magnesium.

The clay supports for this invention should be essentially free of heavy metals, especially iron, or should have a low content of these metals. In general, clays which are suitable for use as catalysts for petroleum cracking or other petroleum processing operations are suitable as supports for the catalysts of this invention.

A preferred clay mineral is bentonite, which contains a major proportion of montmorillonite. (Bentonite is 90% montmorillonite, according to R. K. Iler, "The Colloid Chemistry of Silica and Silicates," Cornell University Press, Ithaca, NY 1955, page 191.) Montmorillonite has an octahedral sheet or layer of alumina in which there may be some replacement of Al by Mg, sandwiched between two tetrahedral silica sheets in which part of the Si is replaced by Al. Montmorillonite has a nominal formula $Al_2O_3 \cdot 4SiO_2 \cdot H_2O + X\ H_2O$. Montmorillonite has a high base exchange capacity.

Another suitable clay mineral is synthetic mica montmorillonite (SMM), a synthetic clay-like aluminosilicate that is generally similar to muscovite mica. SMM is described in a paper by A. C. Wright et al. in Journal of Catalysis 25, 65–80 (1972). Basically, SMM has an octahedral alumina layer sandwiched between two tetrahedral silica layers, with partial substitution of Al for Si in the tetrahedral layers. SMM has base exchange capacity; the ammonium ion is the predominant exhangeable ion in uncalcined SMM.

Other clay minerals having a sheet-like structure, such as kaolinite, can also be used in preparing the catalysts of this invention. The base exchange capacity of kaolinite is significantly lower than that of montmorillonite, but is sufficient for the purpose of this invention. However, clay minerals having a high base exchange capacity are in general preferred.

The clays are preferably activated prior to impregnation with ruthenium in order to increase the surface area and hence the catalyst activity. The preferred activation procedure for most clays is acid treatment following by calcination.

Acid treatment and calcination of clays are known procedures in the art for improving catalyst activity, and acid treatment and calcination conditions known in the art can be used in preparing the clay catalyst. The raw clay can be treated directly with an aqueous mineral acid, such as hydrochloric or sulfuric acid; this differs from the treatment of alkali metal-containing zeolites, which must be converted by ion exchange to the ammonium form and then calcined, instead of being treated directly with acid. Acid treatment and calcination greatly increases the surface area of the clay; raw clays generally have too low a surface area to be suitable as catalysts supports, while acid treated clays typically have BET surface areas greater than 100 square meters per gram and most often greater than 150 square meters per gram, which are very desirable for catalyst use. Also acid treatment reduces iron content and removes alkali metal ions such as sodium, which are detrimental to catalyst activity. Magnesium and part of the aluminum present are also removed by acid treatment, so that an acid treated clay will have a higher silica/alumina ratio than the raw clay from which it was prepared. Acid treated clays also have an appreciable number of hydrogen ion sites which serves to catalyze the hydrolysis of polysaccharides in the carbohydrate starting material to monosaccharides.

Clay minerals which have a substantial quantity of exchangeable ammonium ions such as SMM, can be activated by calcination alone. Calcination decomposes the ammonium ions into hydrogen ions, which provides acid sites. Activated SMM typically has a BET surface area of about 135–160 $m^2/g$, the area depending largely on the temperature of activation.

Ruthenium can be deposited on the clay surfaces by ion exchange of the activated clay with an aqueous solution of a simple ruthenium salt, such as ruthenium trichloride, followed by reduction of the ruthenium to the metallic state. Better results are obtained with a simple ruthenium salt than with a complex ruthenium salt such as a ruthenium ammine salt. Ion exchange may be accomplished by known techniques, e.g. suspending the clay in the aqueous ruthenium salt solution at an elevated temperature and for a time sufficient to effect ion exchange, separating the ruthenium-impregnated clay particles from the solution by conventional means such as filtration, and drying the impregnated clay. This gives the unreduced form of the catalyst, in which the ruthenium is present as a trivalent cation. The ruthenium can then be reduced to the metallic state, either prior to being placed into service, or in situ during hydrogenation of D-glucuronic acid. The latter is preferred, since it requires fewer catalyst preparation steps and is therefore a lower cost operation. When the ruthenium is reduced in situ, the dried catalyst, containing ruthenium in the trivalent state, is suspended in the reaction medium; reduction of the ruthenium with hydrogen occurs prior to hydrogenation of the D-glucuronic acid. When the ruthenium is reduced prior to placing the catalyst into service, such reduction can be carried out either in the dry state, preferably at a temperature of about 100° to 200° C., or in an aqueous solution or slurry at elevated temperature (preferably about 100°–200° C.) and pressure, using hydrogen as the reducing agent in either case.

Ruthenium catalysts comprising a carbon support may be obtained from Engelhard Industries of Newark, New Jersey.

The hydrogenation of the invention is carried out in a solvent, preferably an aqueous solution. Most preferrably, the hydrogenation solvent is water in view of cost, solubility and purity.

Hydrogenation temperatures for the process of the invention may be up to about 130° C., preferably from about 80 to about 120° C. Such conditions have been found to yield a virtually colorless L-gulonic acid product. Below this range, the reaction will proceed too slowly from an economic standpoint while, above the range, the incidence of undesirable by-products will increase. In contrast, hydrogenation of D-glucuronic acid using a nickel catalyst requires a temperature of about 140°–150° C. which results in an L-gulonic acid having a dark brown color as shown in the Comparative Examples which follow.

The hydrogenation process of the present invention may be carried out in high pressure hydrogenation apparatuses known in the art. A typical reactor for this purpose is the stainless steel 1 liter autoclave model CX-1 of Pressure Products Industries of Hatboro, Pa.

Concentrations of the D-glucuronic acid starting material in the reaction may vary from about 20 to about 50% by weight of the solution as a whole. Such concentrations result in a concentrated final product solution after hydrogenation whereby, it has been found, the product may freely crystalize without use of a precipitation solvent such as ethanol.

In a typical hydrogenation according to the invention, the charge of D-glucuronic acid is dissolved with heating in an amount of water equal to about twice the weight of acid. An amount of ruthenium catalyst is then charged with the acid solution of the hydrogenation apparatus. The amount of catalyst will usually be in the range of about 1000 to about 5000:1, the ratio being the weight of starting material to weight of ruthenium in the ruthenium catalyst. Use of a higher or lower ratio would generally be uneconomic in view of too low a reaction rate and unnecessary amounts of catalyst, respectively. After flushing with nitrogen or any inert gas, the space over the reactant is pressurized with about 1000 to 2000 pounds per square inch (psi) of hydrogen depending on the reactor. This upper figure is provided in consideration of the usual reactors which one would use and, therefore, higher $H_2$ pressures could be used if the reactor would permit such safely. The lower figure of 1000 psi is provided as an indication of a condition which results in the process being sufficiently fast from an economic standpoint. The temperature is then increased and the hydrogen pressure monitored. Preferably, the reactant solution is stirred or rocked. When the pressure is seen to drop at an acceptable rate, e.g. about 200 psi drop per hour, the temperature is leveled. This figure will vary widely depending on the reactor and the monitoring pressure. When no further pressure drop occurs, the temperature may be raised to ensure complete reaction but the absence of a pressure drop will usually indicate complete reaction.

Workup of the hydrogenated mixture may be by conventional methods including cooling of the reactor, removal of its contents, filtration to separate catalyst, concentration by rotary evaporation and collection of crystals from mother liquor. If the solution prior to concentration has a slight color, caused by catalyst oxidation, it may be decolorized with a cation exchange resin, such as IR-120 H+ made by Mallinckrodt of St. Louis, Mo., or with Darco brand activated carbon from ICI Americas Inc. of Wilmington, Del. to remove color. The L-gulonic acid may be analyzed for purity by gas-liquid chromatography (GLC), paper chromatography or thin layer chromatography. The thin layer chromatography and/or GLC may also serve to detect unreacted starting material.

EXAMPLE 1

A solution was prepared from 50 grams (gm) of D-glucuronic acid in the D-glucurono-3,6-lactone form of formula (III) and 200 milliliters (ml) of water. The solution was charged, together with 5 gm of 1% Ru on carbon, type C-3190 obtained from Engelhard Industries, into a one liter stainless steel hydrogenation autoclave Model CX-1 obtained from Pressure Products Industries. A pH of 3.4 was observed. Preferably, the hydrogenation should take place at a pH of about 3 to 5. The autoclave was flushed with nitrogen, pressured with hydrogen gas at about 1500 psi and heated to about 120° C. At this temperature, no pressure drop was observed and, as confirmed by the workup of the experiment, this was due to the fact that all or substantially all of the D-glucuronic acid starting material had already been hydrogenated. Increasing the temperature to 130° to 140° C. did result in a pressure increase. It there had been a pressure drop, such would be due to continued reaction and removal of hydrogen from the gas phase.

After cooling the autoclave to room temperature, the contents were removed, filtered and concentrated. The slight greenish color of the concentrated solution, caused by catalyst cations, was removed by passing it through a column loaded with 20 g of IR-120 H+ cation exchange resin. Upon partial evaporation under vacuum, the resin-treated solution yielded 50 gm of L-gulonic acid crystals in the 1,4-lactone form, melting point 181°–3° C. Thin layer chromatography of the L-gulonic acid product showed one spot and no starting material. The absence of starting material was confirmed by GLC.

The results of this experiment confirmed that the hydrogenation of D-glucuronic acid with a ruthenium catalyst had already been substantially complete by the time the temperature had been raised to 120° C. That is, as the temperature of the fully charged autoclave increased from 120° C. to 130° C. and 140° C., no further reaction of hydrogen occurred as evidenced by the fact that the pressure increased in this transition and did not decrease once the upper temperature was achieved.

EXAMPLE 2

The starting material, catalyst and procedures of Example 1 were repeated with the following exceptions. 100 gm of starting material, 200 ml of water and 7.5 gm of a 1% Ru on C catalyst were used. The pH of the charge was found to be 3.5. After heating to 100° C., the pressure was found to be 1850 psi of hydrogen which figure dropped to 1680 psi, while the reactor was held at 100° C., within 30 minutes. After confirming that the 1680 psi figure was a leveling off of the pressure, the temperature was increased to 120° C. and the pressure increased to 1730 psi. The pH of the reactor contents, after cooling to room (ambient) temperature was 3.0. After isolation of the 1,4-lactone of L-gulonic acid by the procedures described in Example 1, the 96.8 gm of product was found by melting point, mixed melting point and infarred spectra to be identical with an authentic sample of 1,4-gulono lactone obtained from ICN Pharmaceuticals of Plainview, N.Y.

EXAMPLE 3

The starting material and procedures described in Example 1 were repeated, with the exception that 100 gm of D-glucuronic acid were reacted, utilizing 3 gm of 1% Ru on K-10 montmorillonite, the support being obtained from United Catalyst, Inc. of Louisville, Kentucky as the catalyst. The supported Ru catalyst was prepared as set forth in Example 1 of U.S. Pat. No. 3,963,789. The pH of the charge was found to be 3.0. At a reaction temperature of 100° C., the initial pressure of hydrogen of 1800 psi dropped and leveled off at 1550 psi. The yield of the first crop of crystals was 62.4 gm which comprised 28.5% by weight of starting material and 69.3% by weight of L-gulonic acid lactone as determined by GLC. A second crop of 4.8 gm of crystals was obtained from the mother liquor by further precipitation and this crop was determined to be of a composition similar to the first.

EXAMPLE 4

A catalyst comprising ruthenium metal on faujasite zeolite was prepared as described in the paragraph bridging Columns 11 and 12 of U.S. Pat. No. 3,963,788.

Example 3 was repeated utilizing 3 gm of the 1% Ru on SK-89 ultrastable faujasite described in the preceding paragraph as the catalyst. The yield of the first crop of crystals was 62.4 gm consisting of 34.5% by weight of starting material and 65.5% by weight of L-gulonic acid lactone as determined by GLC analysis. A second crop of 4.0 gm was obtained from the mother liquor, which crop analyzed as the first crop.

In Examples 2, 3 and 4, the cation exchange resin used to remove green color described in Example 1 was used in a similar manner before partial evaporation and precipitation of the desired product.

The higher yield of the desired D-gulonic acid product in Examples 1 and 2 as compared with Examples 3 and 4 is believed to be due, at least in part, to the superiority of carbon as a support.

COMPARATIVE EXAMPLE 1

The starting material and procedures of Example 1 were repeated with the exception that the catalyst was 5 gm of 20% Ni on Kieselguhr. The catalyst is similar to that described in Example 4 of German Patentschrift No. 618,907 issued Sept. 5, 1935.

The pH of the charged starting material, solvent and catalyst was 3.4. After reaction at 150° C. for 60 minutes, no pressure drop occurred. The autoclave was cooled to room temperature and the contents filtered to yield a dark brown filtrate. The filtrate was treated with 20 gm of IR-120 H+ resin as described in Example 1, and the filtrate from this treatment was stirred for ½ hour with Darco activated carbon, filtered, partially evaporated and precipitated with ethyl alcohol. A GLC analysis of the precipitate showed the product to be 94.6% by weight of L-gulonic acid lactone, 2.15% by weight of pentoses and 3.24% by weight tetroses. Such pentoses and tetroses, which are undesired by-products, were not found in the GLC analysis of the precipitates in Examples 1 to 4.

COMPARATIVE EXAMPLE 2

The starting material, catalyst and procedures of Comparative Example 1 were repeated. However the temperature was initially only taken to 120° C. at which no pressure drops occurred after 19 minutes. The temperature was then raised to 140° C. and over a period of 60 minutes, the pressure dropped from 1930 psi to 1560 psi of hydrogen and leveled off.

After cooling to room temperature, the autoclave was opened and the contents removed and filtered to give a dark brown solution. This solution was worked up as in Comparative Example 1 and the GLC product analysis was similar, specifically the GLC showed significant amounts of pentoses and tetroses.

What is claimed is:

1. A process for the preparation of L-gulonic acid which comprises hydrogenating D-glucuronic acid in a solvent at a temperature up to about 130° C. and in the presence of a ruthenium catalyst.

2. The process of claim 1, wherein said ruthenium catalyst comprises ruthenium and a support therefor.

3. The process of claim 2, wherein said ruthenium catalyst comprises from about 0.1 to about 5% ruthenium metal.

4. The process of claim 2, wherein said support is selected from the group consisting of carbon, an alumino-silicate zeolite or an alumino-silicate clay.

5. The process of claim 4, wherein said support is carbon.

6. The process of claim 1, wherein said temperature is about 80° to about 120° C.

7. The process of claim 1, wherein said solvent is an aqueous solution.

8. The process of claim 7, wherein said solvent is water.

9. The process of claim 1, wherein said D-glucuronic acid is present in a weight ratio, to the ruthenium metal of the ruthenium catalyst, of about 1000 to about 5000:1.

* * * * *

UNITED STATES PATENT AND TRADEMARK OFFICE
CERTIFICATE OF CORRECTION

PATENT NO. : 4,326,072
DATED : April 20, 1982
INVENTOR(S) : Walter M. Kruse and Makram H. Meshreki It is certified that error appears in the above—identified patent and that said Letters Patent is hereby corrected as shown below:

Column 1, line 13, delete "of" and insert --to--.

Column 2, line 46 delete "(II)" and insert --(III)--.

Column 3, line 68, delete "L" and insert --1--.

Signed and Sealed this

Sixteenth Day of November 1982

[SEAL]

Attest:

GERALD J. MOSSINGHOFF

Attesting Officer — Commissioner of Patents and Trademarks